United States Patent [19]

Martel et al.

[11] Patent Number: 4,487,957

[45] Date of Patent: Dec. 11, 1984

[54] PROCESS FOR THE PREPARATION OF ALKYL 4-METHYL-3-FORMYL-PENTEN-1-OATES

[75] Inventors: Jacques Martel, Bondy; Jean Tessier, Vincennes; Jean-Pierre Demoute, Montreuil-sous-Bois, all of France

[73] Assignee: Roussel Uclaf, Paris, France

[21] Appl. No.: 487,283

[22] Filed: Apr. 21, 1983

Related U.S. Application Data

[62] Division of Ser. No. 275,292, Jun. 19, 1981.

[30] Foreign Application Priority Data

Jun. 20, 1980 [FR] France .............................. 80 13733

[51] Int. Cl.³ ............................................ C07C 69/73
[52] U.S. Cl. .................................... 560/177; 549/302; 549/313; 560/168; 560/226; 562/577; 564/250; 564/277; 564/279
[58] Field of Search ................ 560/168, 177; 562/577; 564/250

[56] References Cited

PUBLICATIONS

Lowry, T. H. and Richardson, K. S., *Mechanism and Theory in Organic Chemistry*, Harper and Row, New York, (1976), pp. 456–457.

House, H. O., *Modern Synthetic Reactions*, 2nd ed., W. A. Benjamin, Inc., Menlo Park, Calif., (1972), p. 492.

*Primary Examiner*—Natalie Trousof
*Assistant Examiner*—Bruce D. Gray

*Attorney, Agent, or Firm*—Charles A. Muserlian; Charles A. Muserlian

[57] ABSTRACT

A novel alkyl 4-methyl-3-formyl-penten-1-oate of the formula

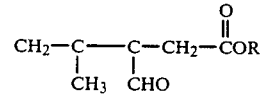

wherein R is alkyl of 1 to 5 carbon atoms and the dotted lines represent a double bond in the 3,4 or 4,5-position and their preparation and novel intermediates therefore and a novel process for the preparation of 4-methyl-3-formyl-pent-3-en-1-oic acid which is an intermediate for the preparation of compounds of the formula

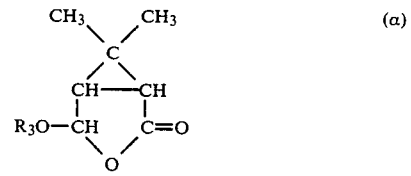

wherein $R_3$ is selected from the group consisting of hydrogen and the residue of an alcohol $R_3OH$ by the process of European Patent Application Ser. No. 0023849 published Feb. 11, 1981, which are used to prepare very active insecticidal esters.

8 Claims, No Drawings

PROCESS FOR THE PREPARATION OF ALKYL 4-METHYL-3-FORMYL-PENTEN-1-OATES

PRIOR APPLICATION

This application is a division of our copending application Ser. No. 275,292 filed June 19, 1981, now abandoned.

OBJECTS OF THE INVENTION

It is an object of the invention to provide a novel esters of formula I and a novel process and novel intermediates for their preparation.

It is another object of the invention to provide a novel process for the preparation of 4-methyl-3-formyl-pent-3-en-1-oic acid.

These and other objects and advantages of the invention will become obvious from the following detailed description.

THE INVENTION

The novel ester compounds of the invention are alkyl 4-methyl-3-formyl-penten-1-oate of the formula

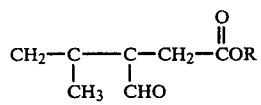

wherein R is alkyl of 1 to 5 carbon atoms and the dotted lines represent a double bond in the 3,4 or 4,5-position.

R is preferably methyl, ethyl, n-propyl, isopropyl and branched or linear butyl and pentyl. Specific preferred compounds of formula I are tert.-butyl 4-methyl-3-formyl-pent-3-enoate and tert.-butyl 4-methyl-3-formyl-pent-4-enoate.

The novel process of the invention for the preparation of compounds of formula I comprises reacting an unsaturated imino compound of the formula

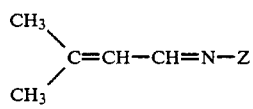

wherein Z is selected from the group consisting of alkyl of 1 to 6 carbon atoms, a hydrocarbon ring, monocyclic aryl and

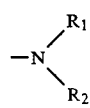

and $R_1$ and $R_2$ are individually alkyl of 1 to 6 carbon atoms in a solvent in the presence of at least one strong base with an alkyl haloacetate of the formula

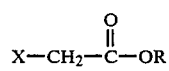

wherein X is a halogen and R is alkyl of 1 to 5 carbon atoms to obtain a compound of the formula

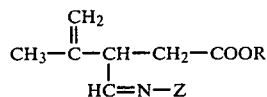

and subjecting the latter to either (a) a double exchange with formaldehyde or (b) hydrolysis in an acid medium to obtain a compound of the formula

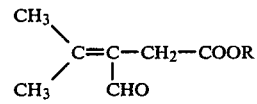

or a compound of the formula

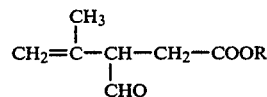

or a mixture of the said compounds.

In a preferred mode of the said process of the invention, the strong base or mixture of strong bases is selected from the group consisting of organometallics such as alkyllithiums or aryllithiums, alkali metal amides, alkali metal alcoholates and alkali metal hydrides and the solvent is selected from the group consisting of aprotic polar solvents such as hexamethylphosphorotriamide, dimethylformamide, tetrahydrofuran and dimethoxyethane alone or in admixture with hydrocarbons. The alkyl haloacetate is preferably the alkyl bromoacetate or chloroacetate wherein the alkyl is methyl, ethyl, propyl, n-butyl, pentyl or tert.-butyl.

The novel intermediates of the invention are the compounds of formula IV and especially preferred is tert.-butyl 4-dimethylhydrazono-3-(propen-2-yl)-butenoate.

The novel process of the invention for the preparation of 4-methyl-3-formyl-pent-3-en-1-oic acid comprises subjecting at least one compound of formula $I_1$ and $I_2$ to acidolysis. Under a preferred embodiment of the said process, the hydrolysis of the ester function is effected with an acid agent or a basic agent. In the case of the tert.-butyl ester of formula I, the hydrolysis may be effected with a strong acid, preferably trifluoroacetic acid, in an anhydrous medium.

4-methyl-3-formyl-pent-3-en-1-oic acid is an intermediate for the preparation of compounds of the formula

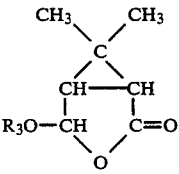

wherein $R_3$ is selected from the group consisting of hydrogen and the residue of an alcohol $R_3OH$ by the process of European patent application Ser. No. 0023849 published July 11, 1981 by reacting 3-formyl-4-methyl-pent-3-ene-1-oic acid under anhydrous conditions with a hydrogen halide in the presence of LiX wherein X is halogen in an organic solvent to obtain a compound of the formula

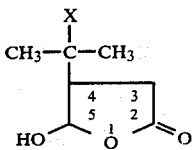

reacting the latter with an achiral alcohol R₁OH to obtain a racemic compound of the formula

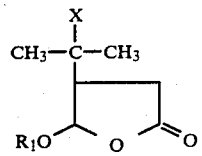

which, together with the compound of formula VI has a trans relation with the 4 and 5 substituents of the tetrahydrofuranone or with a chiral alcohol R₁OH, compound VII will be a mixture of two predictable diastereoisomers which may be separated into the individual isomers by physical methods and then reacting the compound of formula VII in its racemic form when R₁ is achiral or in the form of one of its optically active isomers where R₁ is chiral with a basic agent to obtain the bicyclic compound of the formula

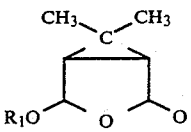

in its racemic form or one of its 2 enantiomeric forms when R₁ is an achiral or a chiral group, respectively, the absolute configuration of the 4-position as well as the following 1- and 5-positions being determined by the sterochemistry of the diasteroisomer of formula VII and optionally subjecting the compound of formula V′ to hydrolysis in an acid medium with total retention of the absolute configurations to obtain a compound of the formula

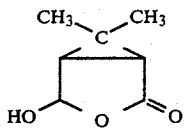

In the following examples there are described several preferred embodiments to illustrate the invention. However, it should be understood that the invention is not intended to be limited to the specific embodiments.

EXAMPLE 1

Tert.-butyl 4-methyl-3-formyl-pent-3-en-1-oate and tert.-butyl 4-methyl-3-formyl-pent-4-en-1-oate

STEP A: Tert.-butyl 4-dimethyl-hydrazono-3-(propen-2-yl)-butenoate

A solution of 21.5 mmoles of butyllithium in cyclohexane was added at −20° to −30° C. to a mixture of 25.8 mmoles of diisopropylamine and 5 volumes of tetrahydrofuran and the mixture was stirred at +20° to 25° C. for 20 minutes. The mixture was cooled to 5° C. and a solution of 17.9 mmoles of 3-methyl-but-2-enal-dimethyl-hydrazone in 2 volumes of tetrahydrofuran was added thereto dropwise. The mixture was stirred at +20° C. for 20 minutes, then cooled to −15° C. and a solution of 23.3 mmoles of tert.-butyl bromoacetate in 2 volumes of tetrahydrofuran was added slowly thereto, after which the mixture stood at −15° C. for one hour. The mixture was poured into an iced monosodium phosphate solution and the mixture was extracted with benzene. The organic phase was evaporated to dryness under reduced pressure and the residue was chromatographed over silica gel. Elution with a 9-1 benzene-ethyl acetate mixture yielded 2.4 g of tert.-butyl 4-dimethyl-hydrazono-3-(propen-2-yl)-butenoate.

IR SPECTRUM (CHLOROFORM)

Absorption at 1645 and 900 cm⁻¹ (CH₂=C<); at 1720 cm⁻¹ (C=0).

NMR SPECTRUM (DEUTEROCHLOROFORM)

Peaks at 1.43 ppm (hydrogens of methyls of tert.-butyl); at 1.73 ppm (hydrogens of methyl α- to methylene); at 2.43–2.61 ppm (hydrogens α- to C=0); at 2.73 ppm (methyls of

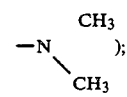

at 3.33 ppm (hydrogen β- to COOH); at 4.8 ppm (hydrogens of

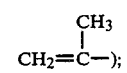

at 6.47–6.55 ppm (hydrogen of —CH=N—).

STEP B: Tert.-butyl 4-methyl-3-formyl-pent-3-enoate and tert.-butyl 4-methyl-3-formyl-pent-4-enoate 50 mg of the product of Step A were added to a mixture of 1.5 ml of acetone, 1 ml of 40% aqueous formaldehyde and 0.1 ml of a 22° Bé hydrochloric acid solution and the mixture was stirred at 20° C. for 7 hours and was extracted with benzene. The organic phase was evaporated to dryness under reduced pressure and the residue was chromatographed over silica gel. Elution with a 9-1 benzene-ethyl acetate mixture yielded a fraction of 20 mg of tert.-butyl 4-methyl-3-formyl-pent-3-enoate (I_A) and 12 mg of tert.-butyl 4-methyl-3-formyl-pent-4-enoate (I_B).

IR SPECTRUM (CHLOROFORM)

Compound I_A: Absorption at 2715 cm⁻¹ (CH of aldehyde); at 1720 cm⁻¹

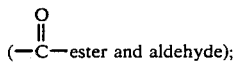

at 1368 cm⁻¹ (tert.-butyl); at 905 cm⁻¹ (CH₂=C<)

Compound I_B: Absorption at 1721 cm⁻¹ (ester carbonyl); at 1662 cm⁻¹ (conjugated aldehyde); at 1631 cm⁻¹ (conjugated —C=C); at 1390 cm⁻¹ (geminal methyls); at 1370 cm⁻¹ (tert.-butyl).

NMR SPECTRUM (DEUTEROCHLOROFORM)

Compound $I_A$: Peaks at 1.45 ppm (hydrogens of methyls of tert.-butyl); at 1.75 ppm (hydrogens of 5—$CH_3$); at 1.92 to 2.2 ppm (hydrogens of methylene α- to carboxyl); at 3.5 ppm (3-hydrogen); at 4.3–8.4 ppm (terminal hydrogens of double bond). Compound $I_B$: Peaks at 1.43 ppm (hydrogens of methyls of tert.-butyl); at 1.97 ppm (hydrogens of 5—$CH_3$); at 2.25 ppm (hydrogens of terminal —$CH_3$); at 3.3 ppm (hydrogens of methylene α- to carboxyl); at 10.1 ppm (hydrogen of aldehyde).

EXAMPLE 2

4-methyl-3-formyl-pent-3-en-1-oic acid

A solution of 0.956 g of tert.-butyl 4-methyl-3-formyl-pent-3-enoate in 8.7 ml of methylene chloride was added at 0° to 5° C. to a mixture of 15.5 ml of trifluoroacetic acid and 20 ml of methylene chloride and the mixture was stirred at 5° C. for 3 hours. Cyclohexane was added to the mixture which was then evaporated to dryness under reduced pressure. The residue was empasted with isopropyl ether to obtain 0.444 g of 4-methyl-3-formyl-pent-3-en-1-oic acid melting at 102° C. The mother liquors were chromatographed over silica gel and elution with a 1-1-1 benzene-acetone-chloroform mixture yielded 40 mg of 4-methyl-3-formyl-pent-3-en-1-oic acid melting at 102° C.

NMR SPECTRUM (DEUTEROCHLOROFORM)

Peaks at 2.0 ppm (5-hydrogens); at 2.26 ppm (hydrogens of 4-$CH_3$); at 3.38 ppm (2-hydrogens); at 10.1 ppm (hydrogen of formyl).

The process was repeated using tert.-butyl 4-methyl-3-formyl-pent-4-enoate to obtain 4-methyl-3-formyl-pent-3-en-1-oic acid.

Various modifications of the products and processes of the invention may be made without departing from the spirit or scope thereof and it is to be understood that the invention is intended to be limited only as defined in the appended claims.

What is claimed is:

1. A process for the preparation of an alkyl 4-methyl-3-formyl-penten-1-oate of the formula

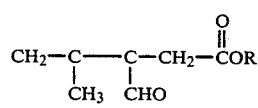

wherein R is alkyl of 1 to 5 carbon atoms and the dotted lines represent a double bond in the 3,4 or 4,5-position comprising reacting an unsaturated imino compound of the formula

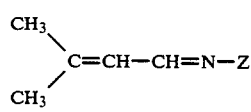

wherein Z is selected from the group consisting of alkyl of 1 to 6 carbon atoms, a hydrocarbon ring, monocyclic aryl and

and $R_1$ and $R_2$ are individually alkyl of 1 to 6 carbon atoms in a solvent in the presence of at least one strong base with an alkyl haloacetate of the formula

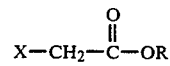

wherein X is a halogen and R is alkyl of 1 to 5 carbon atoms to obtain a compound of the formula

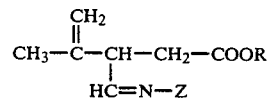

and subjecting the latter to either (a) a double exchange with formaldehyde or (b) hydrolysis in an acid medium to obtain a compound of the formula

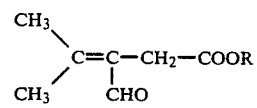

or a compound of the formula

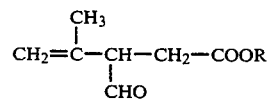

or a mixture of the said compounds.

2. The process of claim 1 wherein the strong base is at least one member of the group consisting of alkali metal hydrides, alkali metal alcoholates, alkali metal amides, alkyllithiums and aryllithiums.

3. The process of claim 1 wherein the solvent for the reaction of the compounds of formulae II and III is selected from the group consisting of hexamethylphosphorotriamide, dimethylformamide, tetrahydrofuran and dimethoxyethane alone or in admixture with hydrocarbons.

4. The process of claim 1 wherein the alkyl haloacetate is selected from the group consisting of alkyl chloroacetate and alkyl bromoacetate wherein the alkyl is selected from the group consisting of methyl, ethyl, n-propyl, n-butyl, pentyl and tert.-butyl.

5. A process for preparation of 4-methyl-3-formyl-pent-3-en-1-oic acid comprising subjecting an alkyl 4-methyl-3-formyl-penten-1-oate of the formula

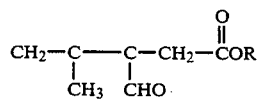

wherein R is alkyl of 1 to 5 carbon atoms and the dotted lines represent a double bond in the 3,4 or 4,5-position to acidolysis.

6. The process of claim 5 wherein the acidolysis is effected with an acid agent or a basic agent.

7. The process of claim 5 wherein R is tert.-butyl and the acidolysis is effected with a strong acid in an anhydrous medium.

8. The process of claim 7 wherein the strong acid is trifluoroacetic acid.

* * * * *

UNITED STATES PATENT AND TRADEMARK OFFICE
CERTIFICATE OF CORRECTION

PATENT NO. : 4,487,957
DATED : Dec. 11, 1984
INVENTOR(S) : JACQUES MARTEL, JEAN TESSIER, JEAN-PIERRE DEMOUTE

It is certified that error appears in the above-identified patent and that said Letters Patent are hereby corrected as shown below:

| Col. | Line | Abstract |
|------|------|----------|
| [57] | | "$CH_2-\underset{\underset{CH_3}{\vert}}{C}-\underset{\underset{CHO}{\vert}}{C}-CH_2-\overset{\overset{O}{\Vert}}{C}OR$" I |
| | | should be |
| | | $--CH_2=\underset{\underset{CH_3}{\vert}}{C}=\underset{\underset{CHO}{\vert}}{C}-CH_2-\overset{\overset{O}{\Vert}}{C}OR\ --$ I |
| 1 | 30 | " " " " " " " " " " " " " " " |
| 5 | Claim 1 | " " " " " " " " " " " " " " " |
| 6 | Claim 5 | " " " " " " " " " " " " " " " |

Signed and Sealed this

*Twentieth* Day of *August 1985*

[SEAL]

*Attest:*

DONALD J. QUIGG

*Attesting Officer*    *Acting Commissioner of Patents and Trademarks*